United States Patent [19]

Mills

[11] Patent Number: 4,608,987
[45] Date of Patent: Sep. 2, 1986

[54] APPARATUS FOR TRANSMITTING ECG DATA

[75] Inventor: Henry E. Mills, Dickinson, Tex.
[73] Assignee: Physioventures, Inc., Houston, Tex.
[21] Appl. No.: 446,638
[22] Filed: Dec. 3, 1982
[51] Int. Cl.$^4$ ............................................. A61B 5/04
[52] U.S. Cl. ...................................... 128/639; 128/644
[58] Field of Search ........................... 128/639–641, 128/643, 644, 783, 798, 799, 802, 803

[56] References Cited

U.S. PATENT DOCUMENTS

| 2,318,207 | 5/1943 | Ellis | 128/644 |
|---|---|---|---|
| 2,409,033 | 10/1946 | Garceau | 128/644 X |
| 2,815,749 | 12/1957 | Friedman | 128/644 |
| 3,409,007 | 11/1968 | Fuller | 128/644 |
| 3,498,291 | 3/1970 | Bunn | 128/644 |
| 3,534,727 | 10/1970 | Roman | 128/644 |
| 3,612,061 | 10/1971 | Collins et al. | 128/799 |
| 4,026,278 | 5/1977 | Ricketts et al. | 128/644 |
| 4,202,344 | 5/1980 | Mills et al. | 128/644 |
| 4,381,012 | 4/1983 | Russek | 128/644 |
| 4,391,279 | 7/1983 | Stein | 128/643 |
| 4,448,199 | 5/1984 | Schmid | 128/639 |

FOREIGN PATENT DOCUMENTS

| 1355600 | 2/1964 | France | 128/644 |
|---|---|---|---|
| 274612 | 7/1951 | Switzerland | 128/644 |

OTHER PUBLICATIONS

Barr, "A Device for Rapid ECG Monitoring", Anaesthesia, vol. 27, No. 1, Jan. 1972, pp. 94–96.

Primary Examiner—Lee S. Cohen
Attorney, Agent, or Firm—Norvell & Associates

[57] ABSTRACT

A vest-like garment is provided comprising a front fabric panel with a plurality of apertures adapted for receiving associated electrodes, a horizontally stretchable rear panel, and a pair of vertically stretchable shoulder straps. Each of the electrodes is biased against the front panel for better electrical engagement with the skin of the user. Leads from each electrode may carry signals to a telephonic transmission unit, which is also equipped with emergency electrode handles.

19 Claims, 6 Drawing Figures

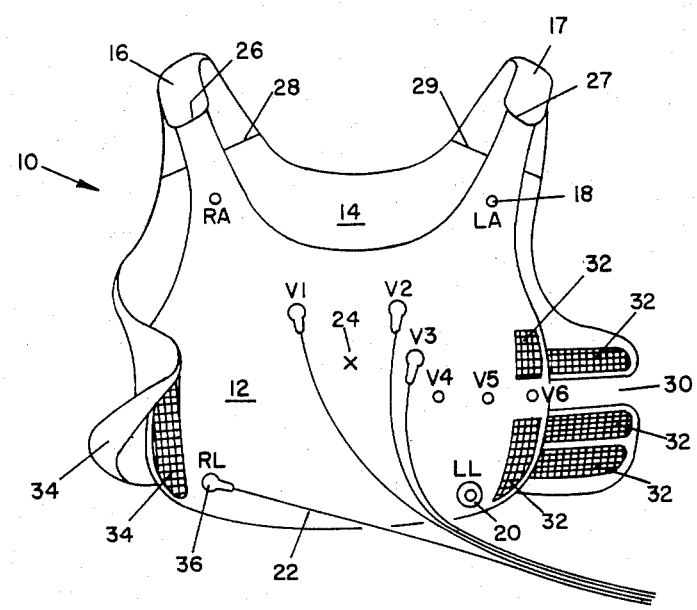
FIG. 1
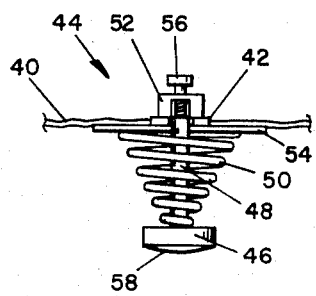
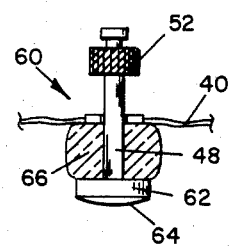
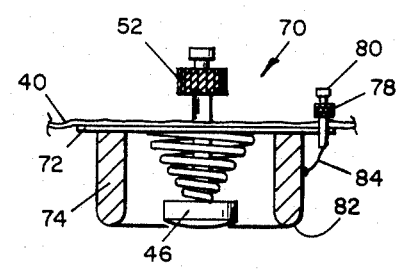
FIG. 2   FIG. 3   FIG. 4

APPARATUS FOR TRANSMITTING ECG DATA

BACKGROUND OF THE INVENTION

The vast majority of electrocardiological testing is performed in a cardiologist's office or the hospital. In either case, a quality electrocardiograph printout generally comprises twelve separate tracings obtained from a predetermined combination of signals from a plurality of electrodes. Trained personnel are required to properly position the electrodes on the patient, and an electrode gel is applied to the skin of the patient to enhance signal clarity. Signals are processed and filtered by conventional electrocardiograph (ECG) equipment, and the graphic output or printout from the ECG equipment may be used by the cardiologist to evaluate and diagnose coronary disorders or establish baseline cardiac data.

The above procedure is both expensive and time consuming, especially when a coronary out-patient must make regular weekly visits to the cardiologist to evaluate coronary recovery or monitor baseline data. Because of the limited mobility of some patients, doctors frequently keep a patient in the hospital for an extended period to perform regular ECG testing.

It has been known for some time that a tremendous time and cost savings could be realized if the untrained patient could generate ECG data without professional assistance. Also, additional savings could be realized if the patient could generate such data at his home or office, and transmit or forward the data to the ECG evaluation equipment at the cardiologist's office or at the hospital. The problem, however, has been that prior art methods and apparatus are not clinically and professionally acceptable to the cardiologist and/or fail to gain patient confidence and approval. Thus, such prior art methods and apparatus have not been widely used and accepted to date.

Prior art garments typically utilize an elastic cloth front portion specifically tailored to the individual patient. U.S. Pat. No. 2,685,881 teaches a rubber strap for holding a single electrode. Single electrodes, however, are simply not capable of generating a desired complete ECG printout necessary for the cardiologist. U.S. Pat. No. 3,409,007 teaches a vest-like garment fabricated from elastic cloth, with the desired plurality of electrodes. The front portion of the panel preferably has a substantial measure of elasticity in at least two orthogonal dimensions, and band-like appendages are provided for the limb electrodes. U.S. Pat. No. 3,534,727 teaches a garment with flexible elastic electrodes, with the electrodes held in contact with the patient's body by the skin tight garment. U.S. Pat. No. 3,525,330 describes an elastic cloth garment with a grid-like pattern for prescribing the location of electrodes. U.S. Pat. Nos. 4,121,575 and 4,202,344 teach an expandable or stretchable non-conductive strip, such as rubber sheeting, for the six precordial electrodes, while the limb lead electrodes may be of the conventional type. As stated for example in U.S. Pat. No. 4,202,344, the front garment material is stretchable so that when the garment is worn by the patient, the electrodes automatically assume the correct anatomic location on the chest, and thus the position of an electrode moves relative to another electrode depending on the degree the support material is stretched. U.S. Pat. No. 3,409,007 indicates that a portion of the front panel may be provided with multiple thickness of elastic cloth to provide "additional resilient stiffness" to that portion of the garment.

Prior art electrodes are frequently of the "wet" type, wherein a gel is used to increase the clarity of the signal from the electrodes. Many types of electrodes have been described in the prior art, but they generally suffer from poor signal clarity or require a gel to increase signal clarity. U.S. Pat. Nos. 2,685,881 and 3,144,018 each depict a crude metal electrode, while U.S. Pat. No. 3,534,727 illustrates a "flexible" electrode. U.S. Pat. No. 4,121,575 describes a hollow construction electrode which permits the introduction of an electrolyte paste or gel, and U.S. Pat. No. 4,202,344 teaches various bell or cup-shaped electrodes, which also may have a passageway for an electrolyte paste or gel, and which may be held against the body of the patient by the stretch of the chestpiece.

Telephonic units for transmitting ECG signals to ECG receiving equipment at the cardiologist's office are described generally in U.S. Pat. No. 3,910,260. More specific apparatus is described in U.S. Pat. No. 3,426,150, which includes a known value modulation signal for calibration of instruments, and a muting circuit to permit speech transmission over the unit. An exercise measuring system and related electronic apparatus are depicted in U.S. Pat. No. 3,802,698, and a portable cardiac monitoring system and method is described in U.S. Pat. No. 3,991,747. Finally, U.S. Pat. Nos. 3,029,808, 3,199,508, and 3,717,141 each depict electrical apparatus and systems for obtaining signals from skin locations on an individual.

These prior art methods and apparatus are difficult to utilize by an untrained patient, do not result in highly reliable and repeatable ECG signals, and do not satisfy the requirements of many cardiologists and patients. The disadvantages of the prior art are overcome by the present invention, however, and improved methods and apparatus are hereinafter provided for obtaining and transmitting ECG data to conventional graphic output equipment.

SUMMARY OF THE INVENTION

A garment is provided for supporting a plurality of body contact electrodes each in a fixed position relative to the other electrodes, comprising a front fabric panel, a horizontally stretchable rear fabric panel, and a pair of vertically stretchable shoulder straps. The electrodes are biased against the front panel for uniformly engaging the skin of the user and thereby enhancing signal clarity and repeatablility. Signals from the electrodes may be forwarded to a doctor's office by a telephonic transmission unit, which is also equipped with emergency electrode handles.

Accordingly, as a feature of the present invention to provide improved methods and apparatus for generating body electrode signals.

It is a further feature of the invention to provide methods and apparatus which may be employed to accurately and repeatably obtain signals from body electrodes.

It is another feature of the invention to provide methods and apparatus for generating body electrode signals which are readily acceptable to users and physicians.

It is still a further feature of the present invention to provide methods and apparatus which may be easily and accurately used by untrained individuals to generate body electrode signals.

It is an additional feature of the present invention to provide a fabric garment for supporting a plurality of body electrodes, with each electrode in a fixed position relative to other electrodes.

Still a further feature of the present invention is to provide a garment for supporting a plurality of body electrodes each biased against the garment and toward the body of the user.

It is still another feature of the present invention to provide a telephonic transmission unit for normally receiving signals from body electrodes, and the transmission unit further comprising electronic handles for generating signals from the user's hand in an emergency situation.

Other and further objects, advantages and features of the present invention will become apparent from the following detailed description wherein reference is made to the figures in the accompanying drawings.

DESCRIPTION OF THE DRAWINGS

FIG. 1 illustrates a front elevation view of a garment according to the present invention.

FIG. 2 is a pictorial representation of an electrode assembly generally shown in FIG. 1.

FIGS. 3 and 4 are pictorial representations of alternate embodiments of the electrode assembly shown in FIG. 2.

DETAILED DESCRIPTION OF INVENTION

Figure 5:
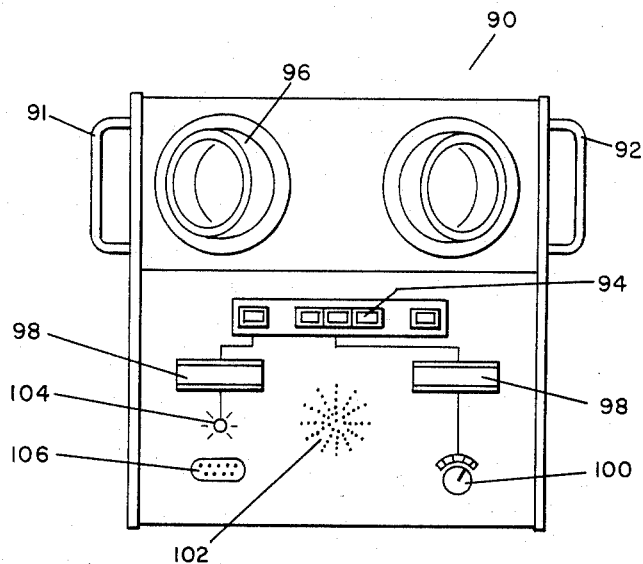
FIG. 5 is a top view of a telephonic transmission unit of the present invention.
Figure 6:
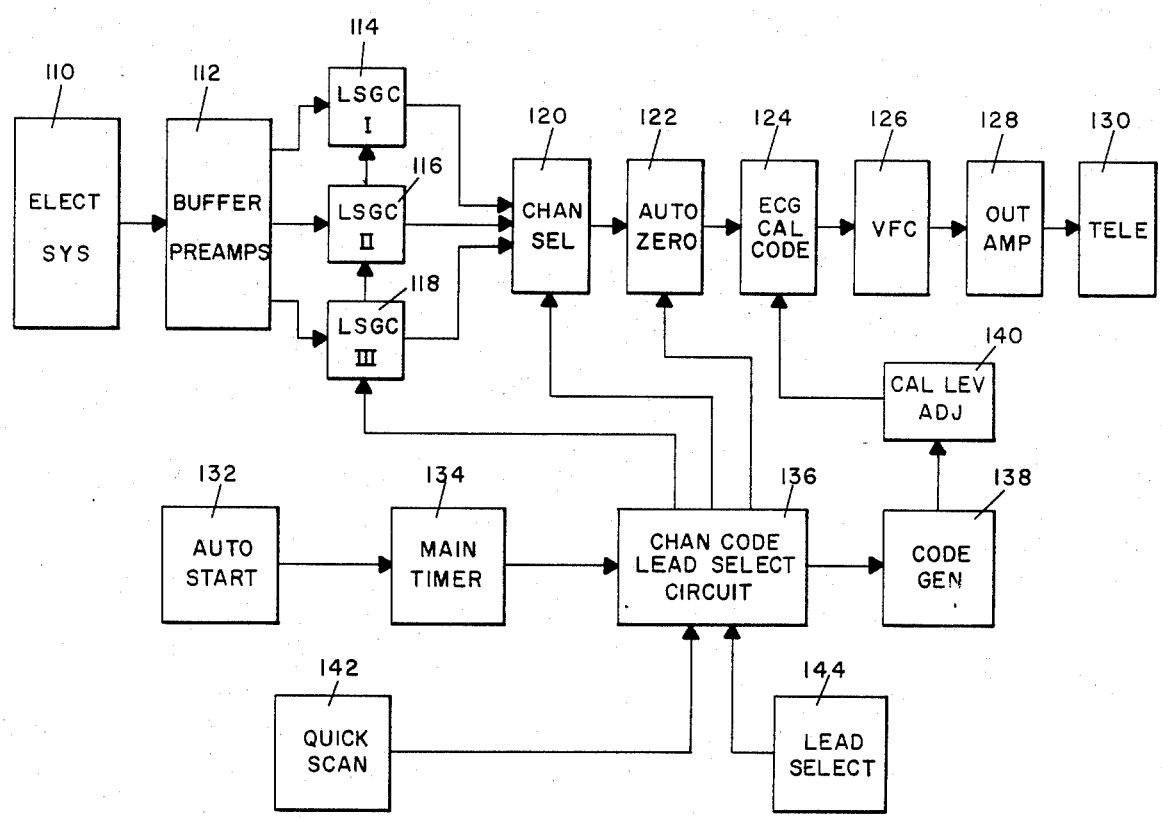
FIG. 6 is a simplified block diagram functionally illustrating the operation of the telephonic transmission unit shown in FIG. 5.

A vest-like garment 10 is shown in FIG. 1, including a front fabric panel 12, a rear fabric panel 14, and a pair of shoulder straps 16, 17. A plurality of apertures 18 in the front panel are each adapted to support an electrode. The vest 10 thus supports not only the precordial electrodes generally referred to as $V_1$, $V_2$, $V_3$, $V_4$, $V_5$ and $V_6$, but also the extremity electrodes associated with the arms (LA, RA) and the legs (LL, RL).

The invention generally includes a vest-like garment 10 which may be sewn or otherwise fabricated from cloth or fabric of various types. A plurality of electrodes 20 are positioned on the garment 10 so that when the garment is worn by the user or patient, the electrodes are electrically conductive with the skin of the user. The electrodes receive signals in the millivolt range from the skin, and may forward such signals via leads 22 to a telephonic transmission unit. Signals from ten electrodes 20 each positioned in its respective aperture 18 may then be forwarded to the doctor's office, and a graphic output from an ECG machine may be used to evaluate cardiac muscle and cardiac nervous condition abnormalities.

The material or fabric of the front portion 12 of vest 10 is non-stretchable and preferably of a single thickness, so that in the plane of the front panel 12 each of the electrodes is fixed in position relative to the other electrodes. The non-stretchable front portion of Applicant's vest is markedly dissimilar to prior art vests which are specifically intended to be stretchable. Moreover, the non-stretchable front portion of Applicant's vest includes apertures for both the four limb electrodes and six precordial electrodes.

The vest 10 of the present invention is preferably not tailored for a specific patient, but rather may be mass fabricated in a few selected sizes, e.g., small, medium and large. Each size vest is suitable for use by a significant portion of the adult population, which substantially reduces the unit cost of the vest. Also, a single size vest 10 may be conveniently used by both male and female patients. Each of the shoulder straps may thus be secured to the front portion by seams 26, 27 and may be secured to the back portion 14 by seams 28, 29.

In order that a selected vest, e.g., a large size vest, properly fits a significant portion of the population, the back portion 14 and shoulder strap 16, 17 are preferably stretchable in at least one direction. More particularly, the back portion 14 of the vest is preferably stretchable in the horizontal direction and non-stretchable in the vertical direction, while the shoulder straps are conversely stretchable in the vertical direction and non-stretchable in the horizontal direction. The back portion 14 thus stretches horizontally to accommodate the girth of the patient, and the shoulder straps stretch vertically to accommodate the chest length of the patient. The front portion 12 also includes an appropriate marking 24 for assisting in properly positioning the front portion with respect to the chest of the patient. Preferably, the front portion 12 may be positioned so that the marking 24 is centered over the xiphoid process of the patient.

As used herein, the term "stretchable material" means material which may be repeatably elongated by patients during normal use of the vest in at least one direction L at least 5% of the length of L without tearing, ripping, or otherwise detrimentally affecting the material. The front portion 12 of Applicant's vest is non-stretchable, meaning that it will not stretch 5% in any direction during normal use without detrimentally affecting the material, and preferably, will stretch less than 3% in any direction. To the limited extent that the front portion 12 is stretchable, it is also elastic, meaning that it will return to substantially its original size when the stretching force is terminated.

As used herein, a horizontally stretchable material means material which is stretchable in the horizontal direction when the material has been properly donned by the patient and the patient is in an upright position. A vertically stretchable material is one which is similarly stretchable in a vertical direction when the material has been so donned by the patient in an upright position. The shoulder straps 16, 17 are thus generally vertically stretchable but are not horizontally stretchable when the vest 10 is being worn by a patient.

FIG. 1 also illustrates that the front portion 12 may be secured on one side to the back portion 14. Thus, one side e.g., the right side, of the back portion may be sewn to the right side of the front portion. Alternatively, the right side of the front and back portions may be secured by Velcro ™ material 34 so that these portions may normally remain secured when the vest is donned and taken off by the patient, but may also be taken apart and re-secured if desired each time the vest is donned by the patient. The other side of the garment (left side) must generally be resecured by the patient after the vest is donned and separated to conveniently take off the vest. A Velcro ™ material 32 may thus be sewn or glued to the left side of both the front portion 12 and the back portion 14. Preferably, the left side of the back portion includes a gap 30 for the $V_6$ electrode, so that securing the left side of the front and back portions do not interfere with the electrode in the $V_6$ aperture or the lead 22 from the $V_6$ electrode.

It will be understood that the front portion 12 includes ten apertures for corresponding electrodes, although only a portion of one such electrode 20 is shown in the LL position in FIG. 1. Several of the other apertures shown in FIG. 1 are covered by a conventional snap-on lead cap 36, which electrically connect the electrodes 20 to a respective lead 22. As explained further below, the lead caps are readily removable from the electrodes 20, and the electrodes 20 may also be easily removed from the front portion 12 of the vest, so that the vest 12 may be laundered or cleaned without adversely affecting the electrodes or leads.

FIG. 2 is a pictorial representation of one embodiment of an electrode 20 which may be used in the vest 10. As previously explained, each of the electrodes 20 is positioned within a respective aperture 18 in the front portion 12. The front portion 12 in the area of each aperture 18 is preferably a single thickness, non-stretchable material 40 identical to the material of the remaining portion of the front portion 12. If desired, a grommet 42 may be secured to the material 40 so that the material would be less likely to tear in the area of the aperature 18.

As shown in FIG. 2, the electrode assembly comprises an electrode contact tip 46 which may be disc-shaped, an electrode post 48 secured to the tip 46, a biasing means or spring 50 positioned between the material 40 and the tip 46, and an electrode nut 52 which may be threaded to the end of the post 48. If desired, a reenforcement material or washer 54 may be positioned between the material 40 and the spring 50 to prevent the spring from inadvertently protruding through the material 40.

The biasing means 50 is provided for enhancing electrical conductivity between the skin of the patient and the electrode tip 46. Thus, neither the elasticity of the material 40 nor an electrode gel is required to make good electrical contact with the skin. The tip 46 and the post 48 may be fabricated from any conductive material, such as stainless steel or conductive silicone.

With respect to the axis of the cylindrical post 48, the electrode tip is axially movable into engagement with the skin of the patient, and is axially biased against the material 40 and toward the skin by the biasing means 50. The post 48 is generally between $\frac{3}{8}''$ and $1\frac{1}{2}''$ in length, and preferably between $\frac{1}{2}''$ and $1''$ in length, which provides sufficient axial movement for the tip 46 relative to the material 40. Also, the biasing means or spring 50 should generally be between 1 lb. per inch and 12 lbs. per inch, and preferably between 2 lbs. per inch and 8 lbs. per inch, so that the electrode tip will be sufficiently biased into engagement with the skin of the patient without discomfort to the patient.

The nut 52 may be threaded to the post 48, and serves to retain the electrode assembly 44 in the aperture 18. The nut may, of course, be easily unthreaded from the post 48 so that the remainder of the assembly may be removed from the vest. The nut 52 may be fabricated from a suitable conductive material, such as stainless steel.

The nut 52 also includes a clip fitting 56 so that a Y-type electrical clip may be snap fitted to the nut. If an O-type electrical clip is utilized, the nut assembly may be unthreaded and the O-clip placed between the base of the nut and the post 48, and the nut rethreaded to the post. Thus, the nut 52 is adapted for use with various types of electrical clips. The electrode tip 46 may include a slightly convex outer surface 58 for engagement with the skin. The convex surface 58 may also be grooved or serrated to enhance good electrical contact with the skin.

FIG. 3 depicts an alternate embodiment electrode assembly which may be used with the vest 10 of the present invention. Electrode assembly 60 is shown in a slightly compressed position with respect to material 40, typical of its position when the vest is being worn by a patient and the electrode tip 62 is in contact with the skin. Electrode assembly 60 may include a metal post 48 and nut 52 identical to the same numbered components in FIG. 2.

The electrode tip 62 including a concave surface 64 may be formed of conductive silicone or other non-metallic conductive material, which may be molded to the post 48. Alternatively, the tip 62 may be fabricated from stainless steel and coated with conductive silicone so that only the convex surface 64 is formed from silicone. One benefit of using a conductive non-metallic material for the electrode tip is that the user is less likely to feel the "chill" normally experienced when metal contacts the skin, since the material is not as thermally conductive as metal.

FIG. 3 also depicts an alternate biasing means, which may be a cylindrical-shaped charcoal ester foam material with a hole for the post 48. As shown in FIG. 3, the foam 66 is somewhat compressed and therefore bulges outwardly slightly. The foam is, of course, elastic, and serves to bias the tip 62 away from the material 40. Although the foam 66 may serve as a biasing means, the spring 50 is more durable and can be easily manufactured within the desired biasing pressure limits previously discussed.

FIG. 4 depicts another embodiment of electrode assembly according to the present invention. Electrode assembly 70 includes a post with an electrode tip 46, and a spring as previously described, and shown in FIG. 4 in a slightly compressed position. The electrode assembly 70 includes a conductive silicone outer ring member 74. The conductive ring member 74 may be electrically connected to connector assembly 78 by lead 84, which may be mechanically fastened or glued to the ring 74. The connector assembly 78 also includes tip 80, which may be identical to tip 56 so that the member 36 may be selectively snapped over and connected electrically to either nut 52 or assembly 78. An enlarged reinforcement pad 72 may be used with the electrode assembly shown in FIG. 4, so that the pad 72 covers the base of the ring member 74 and provides reinforcement for the connection assembly 78.

The ring member 74 has an internal diameter at least as great as the outer diameter of the biasing means. The convex tip surface 82 of the ring 74 is designed to engage the skin of the patient, and is closer to the material 40 than the electrode tip 46 when the biasing means is in its normal (uncompressed) position. Thus the surface 82 serves as a stop means, so that each electrode tip will be in the same position relative to the material, and thus the spring of each electrode assembly will be compressed to the same extent and pressure, when the tip of each electrode assembly is in engagement with the skin of the patient.

In most instances, the ring 74 serves the above described "stop" function, which increases signal uniformity from the various electrodes on the vest, but the signals are transmitted to leads through the electrode tip 46, the post, and the nut 52. However, if a poor signal is obtained from the "internal" electrode, the patient may switch the lead to the alternate electrode post 78, so that signals are obtained through the outer conductive silicone electrode 74.

A further advantage of the electrode assembly shown in FIG. 4 is that a normal and a "backup" electrode are both located in the same approximate anatomical position, since the center for each electrode tip, when engaged with the skin, is at approximately the same point, i.e., aligned with the axis of the electrode post. Thus a single electrode assembly is provided with a primary and backup electrode contact tip, each with the same approximate geometric center relative to the axis of the post 48. The patient can easily switch from one electrode tip to the other electrode tip of a single assembly by moving the cap 36 to the other connector. Moreover the outer ring electrode tip may serve as a stop to limit axial movement of the inner electrode tip to a predetermined valve when the vest is worn by the patient. With the electrode assembly shown in FIG. 4, automatic sensing switch circuitry may be included for automatically selecting the electrode tip (either the primary or the back-up contact tip), which makes the better electrical contact with the patient's skin.

Although it is conceivable that a stretched material may act as a biasing means against an electrode, it has been found that the electrode assembly tends to occasionally twist and buckle under when a material is used as a biasing means. In order that the electrode tip 46 and post 48 move radially, i.e., substantially along the axis of the post, a separate biasing means such as a coil spring is provided according to the present invention between the material and the electrode tip. In the embodiments herein described, the tip 46 tends to move away from and toward the material 40 along line substantially aligned with the axis of the electrode post, thereby causing good electrical contact with the skin and resulting in the desired high reliability of the electrode assembly.

FIG. 5 depicts a typical telephonic transmission unit according to the present invention, which may be used in conjunction with the vest and electrode assemblies herein described for transmitting data to evaluation equipment. Transmission unit 90 may be somewhat boxed-shaped, with handles 91, 92 extending out each side of the unit. A series of operational push buttons 94 are provided on the top of the unit, which are described in further detail below. Rubber foam cups 96 are also provided up on the top near the back of the unit for receiving a typical telephone receiver. One or more battery compartments 98 are provided for powering the transmission unit, and a lead select switch 100, a speaker 102, an "on" light 104, and a female connector 106 for the leads from the electrode assemblies are all provided on the front of the unit and in easy access to the user.

One of the benefits of the transmission unit 90 is that the handles 91, 92 also serve as emergency electrode handles. For instance, if a patient thought he might be having a coronary disorder while not wearing the vest, he could grab the handles 91, 92 with his hands and transmit data to the cardiologist's office. Although the readings from the electrode handles 91, 92 would only be single channel information corresponding to the RA, LA electrodes, the information may be particularly relevant in that it reflects abnormal conditions. Thus, in an emergency situation, the user may dial the emergency phone number, place the receiver on the cups 96, engage the "quick scan" push button, and hold the handles 91, 92 on the side of the unit to transmit single channel ECG information to the cardiologist's office.

FIG. 5 depicts a typical logic diagram for the electronic circuit associated with the telephonic unit 90. The electrode system 110 consists of the ten electrodes placed on the vest and the two handle electrodes. The handle electrodes correspond to the RA and LA electrodes, and are electronically in parallel with those electrodes. When the vest is donned by the patient, no signals from the handle electrodes are generated since the handle electrodes are not in contact with the skin. On the other hand, when signals from the handle electrodes are generated, no signals from the vest are generated. Preferably, the cable with the leads to the connector 106 is unplugged so that the RA and LA electrode leads will not add "noise" to the signals from the handle electrodes.

The signals from the electrode system 110 represent the normal diagnostic lead positions LA, RA, LL, RL, and $V_1$–$V_6$ (with the handle electrodes in parallel with the RA and LA leads). These signals are fed to the buffer preamps 112, which reduces noise, buffers the signals and provide a fixed gain or amplitude increase for the signals. The RA, LA, LL, RL, $V_1$ and the $V_4$ signals are received by the multiplexer and summing amplifier 114, which outputs the conventional I, aVr, $V_1$, and $V_4$ signals in the named sequence. Similarly, the RA, LA, LL, RL, $V_2$ and $V_5$ signals are received by multiplexer and summing amplifier 116 and are output in the order II, $aV_1$, $V_2$, and $V_5$, while the RA, LA, LL, RL, $V_3$, and $V_6$ signals are output as III, aVf, $V_3$, and $V_6$ from the multiplexer and summing amplifier 118. These signals are received by the channel selector 120, which outputs the data in single channel sequence. The output is received by auto zero 122 which resets the output to zero at the beginning of each lead record to compensate for electrode or circuitry offsets. The signals are then fed to ECG/Calibration Code Select 124, which selects between the ECG signals or the calibration code signals. The signals are thereafter converted from analog ECG and calibration signals to frequency modulated signals, which are input to the output amplifier 128, and then to the speaker which generates the FM acoustic analog signals that couple to the telephone system 130. Thus, the transmission unit generates an acoustic signal representative of the signal received by the electrode from the skin of the user.

The output from the electronic transmission unit is preferably I, aVr, $V_1$, $V_4$, II, $aV_1$, $V_2$, $V_5$, III, aVf, $V_3$, and $V_6$. This sequence, although not conventional, is preferable since the graphic output in that same sequence requires only two cuts in order that the data may be graphically displayed in the desired order for the cardiologist. Thus, the electronic transmission unit arranges the ECG data so that it may be output in a sequence which more precisely conforms to the sequence normally desired by the cardiologist.

The telephonic transmission unit is typically energized by depressing first the auto and then the start buttons 132. This selection starts the main timing oscillator circuit 134 to generate control pulses to initiate the ECG sequence cycle and the control pulses for the lead changes. The channel code/lead select circuit 136 generates a digital code for each lead record, and sends control signals to the multiplexer and summing amplifiers 114, 116, 118, the channel selector 120, the auto zero 122, and code generator 138. The calibration level adjusts 140 keeps the calibration code at a selected value, e.g., one millivolt, which is a calibration code fed to the ECG/Calibration Code Select circuit 124. As desired, a start/stop command circuit (not depicted) may also be provided to allow abortion of the auto cycle.

In normal operations, the user dons the vest with the ten electrodes, plugs the cable with the electrode leads into the female receptable 106 on the telephonic transmission unit 90, and depresses the auto and then the start buttons to begin the normal ECG test sequence. At the end of the test sequence, the doctor may inform the patient through the speaker 102 provided on the telephonic transmission unit that additional information is desired from a certain lead, e.g., the $V_4$ lead. The patient may then depress the lead select push button and dial the thumbwheel 100 to the $V_4$ position, so that data from only the electrode or electrodes corresponding to that position would again be received and transmitted to the doctor's office. After the test is complete, the patient will turn the transmission unit off and unplug the cable from the receptacle 106 of the telephonic transmission unit. If desired, the patient may continue to wear the vest 10 under his normal clothing and resume other activities, or may elect to also remove the vest. If the patient believes he is having a coronary disorder and does not have time or elects not to put on the vest, he may depress the quick scan button 142 and hold the handles 91, 92 which will transmit single lead information to the cardiologist's office corresponding to the RA, LA electrodes.

The present invention may thus be used to transmit desired twelve lead diagnostic ECG information to evaluation equipment, display equipment, and/or recording equipment. The signals from the electrodes may also be transmitted to such equipment by electromagnetic waves, or recorded on magnetic tape.

It is apparent the present invention is one well adapted to obtain all the objects and advantages above set forth together with other advantages which will become obvious and inherent from the description of the process and apparatus itself. It will be understood that certain combinations an subcombinations are of utility and may be obtained without reference to other features and subcombinations. This is contemplated by and is within the scope of the present invention. Since many possible embodiments may be made of this invention without departure from the spirit or scope thereof, it needs to be understood that all matters herein set forth and in the accompanying drawings are to be interpreted as illustrative and not in a limiting sense.

What is claimed is:

1. A skin electrode assembly comprising:
a front fabric panel having a plurality of apertures each in a predetermined pattern with respect to said other apertures for placement over the chest of the patient;
a plurality of electrodes each associated with a respective one of said apertures; and
each of said electrodes including
(a) a shaft at least partially within a respective aperture on said front panel and having a shaft axis;
(b) an electrode tip affixed to one end of said shaft for engagement with the skin of the patient;
(c) said shaft movable within said aperture and with respect to said front panel in a direction along said shaft axis;
(d) a stop at the other end of said shaft securing said shaft and electrode tip to said panel;
(e) biasing means adjacent said shaft between said front panel and said electrode tip for biasing said electrode tip into engagement with the skin of the patient;
(f) a ring-shaped member generally encompassing said shaft and having a contact surface for limiting axial movement of said electrode tip to a predetermined extent;
(g) said electrode tip movable outwardly by said biasing means from said fabric panel beyond said contact surface;
(h) an electrode connector electrically connected to said ring-shaped member; and
(i) said ring-shaped member is conductive for transmitting signals from the skin to the electrode connector.

2. An electrode assembly as defined in claim 1, wherein the center of said ring-shaped member is substantially aligned with the center of said electrode tip.

3. An electrode assembly as defined in claim 1, wherein said biasing means is a coil spring in the range of from 1 pound and to 12 pounds per inch.

4. An electrode assembly as defined in claim 3; further comprising:
a reinforcement material between said fabric panel and said spring for providing support to said spring.

5. An electrode assembly as defined in claim 1, wherein said biasing means is an elastic foam material.

6. An electrode assembly as defined in claim 1, wherein said electrode tip includes a convex tip surface for engagement with the skin of the patient.

7. A skin electrode assembly adapted to be removably secured to a fabric panel to be placed over the chest of a patient and having an electrode receiving aperture, comprising:
a shaft having a central axis for placement within said aperture;
an electrode tip affixed to one end of said shaft for engagement with the skin of the patient;
said shaft movable within said aperture in a direction along said shaft axis;
a stop at the other end of said shaft for securing said shaft and said electrode tip to said fabric panel;
biasing means adjacent said shaft for biasing said electrode tip into engagement with the skin of the patient;
a ring-shaped member generally encompassing said shaft and having a contact surface for limiting axial movement of said electrode tip to a predetermined extent;
said electrode tip is movable outwardly by said biasing means from said fabric panel beyond said contact surface;
an electrode connector electrically connected to said ring-shaped member; and
said ring-shaped member is conductive for transmitting signals from the skin to said electrode connector.

8. A skin electrode member as defined in claim 7, wherein the center of said ring-shaped member is substantially aligned with the center of said electrode tip.

9. A skin electrode member as defined in claim 7 wherein said biasing means is a coil spring in the range of from 1 pound to 12 pounds per inch.

10. A skin electrode member as defined in claim 7, wherein said biasing means is an elastic foam material.

11. Apparatus for conducting tests of a patient's electrical potential at the skin, comprising:
- a plurality of body electrodes for engagement with the patient's skin;
- a front fabric panel including a plurality of apertures receiving associated portions of said body electrodes;
- a horizontally stretchable and vertically inelastic back panel;
- securement means for repeatedly securing and separating at least one side of said front fabric panel from said back fabric panel;
- a pair of vertically stretchable shoulder straps each secured at one end to an upper portion of said front fabric panel and at the other end to an upper portion of said back panel; and
- said front fabric panel being inelastic for repeatably maintaining each of said body electrodes in a fixed position relative to other of said body electrodes.

12. Apparatus as defined in claim 11, wherein said plurality of body electrodes includes a plurality of precordial body electrodes and a plurality of extremity body electrodes, and said front fabric panel supports said plurality of precordial body electrodes and said plurality of extremity body electrodes.

13. Apparatus as defined in claim 11, wherein said front fabric panel further includes a designated alignment point for properly positioning said front panel relative to the external notch of the patient.

14. Apparatus as defined in claim 11, further comprising:
- biasing means between said front panel and a skin contact end of each of said plurality of electrodes for biasing each of said electrodes into engagement with the skin of the patient.

15. Apparatus as defined in claim 11, wherein each of said plurality of electrodes comprises:
- a shaft at least partially within a respective aperture on said front panel and having a shaft axis;
- an electrode tip affixed to one end of said shaft for engagement with the skin of the patient;
- said shaft movable within said aperture and with respect to said front panel in a direction along said shaft axis;
- a stop at the other end of said shaft securing said shaft and electrode tip to said panel; and
- biasing means adjacent said shaft between said front panel and said electrode tip for biasing said electrode tip into engagement with the skin of the patient.

16. Apparatus as defined in claim 15, wherein said biasing means is an elastic foam material.

17. Apparatus as defined in claim 15, further including:
- a ring-shaped member generally encompassing said shaft and having a contact surface for limiting axial movement of said electrode tip to a predetermined extent;
- said electrode tip is movable outwardly by said biasing means from said fabric panel beyond said contact surface;
- an electrode connector electrically connected to said ring-shaped member; and
- said ring-shaped member is conductive for transmitting signals from the skin to said electrode connector.

18. A skin electrode assembly adapted to be secured to a panel having an electrode receiving aperture, comprising:
- a shaft having a central axis for placement within said aperture;
- an electrode tip affixed to one end of said shaft for engagement with the skin of the patient;
- said shaft movable within said aperture in a direction substantially along said shaft axis;
- biasing means adjacent said shaft for biasing said electrode tip outwardly into engagement with the skin of the patient;
- a conductive ring-shaped member generally encompassing said shaft and having a skin contact surface for engagement with the skin of the patient and limiting movement of said electrode tip to a predetermined extent; and
- an electrode connector electrically connected to said ring-shaped member.

19. An electrode assembly as defined in claim 18 further comprising:
- a stop at the other end of said shaft for securing said shaft and said electrode tip to said panel.

* * * * *